United States Patent
Yamoto et al.

(10) Patent No.: US 9,126,014 B2
(45) Date of Patent: Sep. 8, 2015

(54) FISTULA CATHETER

(71) Applicant: Covidien LP, Mansfield, MA (US)

(72) Inventors: Natsuko Yamoto, Shizuoka (JP);
Shigeaki Funamura, Shizuoka (JP)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/347,857

(22) PCT Filed: Sep. 28, 2012

(86) PCT No.: PCT/US2012/057759
§ 371 (c)(1),
(2) Date: Mar. 27, 2014

(87) PCT Pub. No.: WO2013/049464
PCT Pub. Date: Apr. 4, 2013

(65) Prior Publication Data
US 2014/0336585 A1    Nov. 13, 2014

(30) Foreign Application Priority Data
Sep. 29, 2011   (JP) .................. 2011-213755

(51) Int. Cl.
*A61M 25/02* (2006.01)
*A61M 25/00* (2006.01)
*A61M 39/02* (2006.01)
*A61J 15/00* (2006.01)

(52) U.S. Cl.
CPC ............ *A61M 25/02* (2013.01); *A61J 15/0042* (2013.01); *A61J 15/0065* (2013.01); *A61M 25/0009* (2013.01); *A61M 25/0097* (2013.01); *A61M 39/0247* (2013.01); *A61J 15/0015* (2013.01); *A61J 15/0092* (2013.01); *A61M 2025/0233* (2013.01); *A61M 2039/0255* (2013.01); *A61M 2039/0261* (2013.01); *Y10T 29/49826* (2015.01)

(58) Field of Classification Search
CPC ............ A61M 25/02; A61M 39/0247; A61M 25/0097; A61M 25/0009; A61M 2039/0255; A61M 2039/0261; A61M 2025/0233; A61J 15/0065; A61J 15/0042; A61J 15/0092; A61J 15/0015; Y10T 29/49826
USPC ........................................ 604/96.01, 101.02
See application file for complete search history.

(56) References Cited

U.S. PATENT DOCUMENTS

| 4,983,167 | A | * | 1/1991 | Sahota | 606/194 |
| 5,447,497 | A | | 9/1995 | Sogard et al. | |
| 5,738,653 | A | * | 4/1998 | Pinchuk et al. | 604/96.01 |
| 5,836,924 | A | | 11/1998 | Kelliher et al. | |
| 5,997,546 | A | * | 12/1999 | Foster et al. | 606/108 |

(Continued)

FOREIGN PATENT DOCUMENTS

| EP | 2226090 A1 | 9/2010 |
| WO | 02/087492 A1 | 11/2002 |

OTHER PUBLICATIONS

WO2006/129419, Tamenori et al., date of publication: 2006.*

(Continued)

*Primary Examiner* — Manuel Mendez (57) ABSTRACT

A fistula catheter in which an intracorporeal fixing part comprises an inner balloon and an outer balloon is disclosed, whereby it is possible to prevent removal from the fistula by means of the inner balloon, even if the outer balloon deflates.

11 Claims, 7 Drawing Sheets

(56) References Cited

U.S. PATENT DOCUMENTS

| | | | |
|---|---|---|---|
| 6,019,746 A | 2/2000 | Picha et al. | |
| 6,132,397 A * | 10/2000 | Davis et al. | 604/101.02 |
| 6,254,570 B1 * | 7/2001 | Rutner et al. | 604/101.02 |
| 6,878,130 B2 | 4/2005 | Fournie et al. | |
| 2002/0032406 A1 * | 3/2002 | Kusleika | 604/101.02 |
| 2005/0113858 A1 | 5/2005 | Deutsch | |
| 2006/0205992 A1 * | 9/2006 | Lubock et al. | 600/3 |
| 2008/0119793 A1 | 5/2008 | Adams et al. | |
| 2010/0057013 A1 | 3/2010 | Harada | |
| 2010/0081991 A1 | 4/2010 | Swisher | |

OTHER PUBLICATIONS

European Search Report dated Dec. 2, 2014 for corresponding European Application No. 12834880.2.
International Search Report and Written Opinion dated Mar. 29, 2013 for corresponding PCT Application No. PCT/US2012/057759.
International Preliminary Report on Patentability dated Apr. 1, 2014 for corresponding PCT Application No. PCT/US2012/057759.
Notification of Reasons for Refusal issued by the Japanese Patent Office, mailed May 12, 2015, for corresponding Japanese Application No. 2011-213755.

* cited by examiner

FISTULA CATHETER

FIELD

The present invention relates to a fistula catheter used to supply fluids such as liquid food or nutrients into an internal organ of a patient.

BACKGROUND

People with a reduced function for ingesting food orally under their own power due to advanced age or illness (referred to below as "patients") are supplied with fluids such as liquid food or nutrients using a fistula catheter.

When water is used in a fistula catheter employing a balloon, the water introduced into the balloon can leak out spontaneously, deflating the balloon, and the balloon may deteriorate and rupture due to contact with bodily fluids or the substance being supplied into the internal organ, and the fistula catheter may undesirably be removed from the fistula. In such cases, the fistula often closes up in a matter of hours so it may no longer be possible to reinsert the fistula catheter. It therefore becomes necessary to form a fistula again. To prevent such an occurrence, an arrangement has been proposed in U.S. Patent Application Publication No. 2008/0119793 A1 in which a reinforcing material is embedded inside the balloon so that the balloon is less likely to deteriorate or rupture.

SUMMARY

However, there are problems with the abovementioned conventional catheter in that it is difficult to produce because a reinforcing material is embedded inside the film-like balloon. Furthermore, the strength of the main part of the balloon can be increased, but this cannot go as far as increasing the strength of the connection between the balloon and the supply tube. The problem mentioned above therefore occurs if water escapes from this portion due to deterioration.

The present invention advantageously provides a fistula catheter in which the intracorporeal fixing part comprises an inner balloon and an outer balloon, whereby it is possible to prevent removal from the fistula by means of the inner balloon, even if the outer balloon deflates. It should be noted that in the following description of the constituent features of the present invention, the reference symbols for corresponding parts in a mode of embodiment are disclosed in parentheses in order to facilitate an understanding of the present invention, but the constituent features of the present invention should not be interpreted as being limited to what is represented by the corresponding parts from the mode of embodiment which are denoted by the reference symbols.

One or more aspects of the present invention can be directed to a fistula catheter to be disposed in a fistula of a patient. One or more embodiments pertinent to one or more such aspects can involve a catheter comprising an extracorporeal fixing part configured to be disposed on the abdominal wall surface-side of the fistula; a supply tube comprising a tubular element joined to the extracorporeal fixing part, and having a tip-end section, and a main lumen and a sub-lumen in a peripheral wall thereof; and an intracorporeal fixing part at an outer periphery of the supply tube and proximate the tip-end section. The intracorporeal fixing part can comprise, in one or more embodiments of the invention, an inner balloon and an outer balloon outside of the inner balloon, a first one-way valve disposed between the sub-lumen and the inner balloon, and a second one-way valve disposed between the sub-lumen and the outer balloon. The inner balloon is in communication with the sub-lumen through the first one-way valve and the outer balloon is in communication with the sub-lumen through the second one-way valve. The fistula catheter, in one or more embodiments of the invention, can further comprise an injection port and a second injection port in the sub-lumen. The first one-way valve, in one or more embodiments of the invention, is disposed in the first injection port. The second one-way valve, in one or more embodiments of the invention, is disposed in the second injection port. The outer balloon is typically comprised of a material that is more stretchable than the inner balloon material comprising the inner balloon. The inner balloon can have fixed or maximum inflation size. Each of the inner balloon and the outer balloon can be adhesively fixed to the supply tube. In use, when each of the inner balloon and the outer balloon is inflated, a space is formed therebetween.

One or more aspects of the invention can be directed to a method of fabricating a fistula catheter to be disposed in a fistula of a patient. The method can comprise providing a supply tube having wall part, a main lumen defined therein, and a sub-lumen within the wall part, the sub-lumen having a first port and a second port on the wall part proximate a tip-end section of the supply-tube; securing an extracorporeal fixing part to the supply tube, the extracorporeal fixing part configured to be disposed on an abdominal wall surface-side of a fistula; securing an inner balloon to the wall part of the supply tube, the inner balloon defining an internal volume in communication with the sub-lumen through the first port; and securing an outer balloon to the wall part of the supply tube, the outer balloon defining an internal volume in communication with the sub-lumen through the second port and enclosing the inner balloon. The method can further comprise securing a first one-way valve in the first port and securing a second one-way valve in the second port.

The fistula catheter (A) according to one or more aspects of the present invention, can comprise an extracorporeal fixing part (10) which is disposed on the abdominal wall surface-side of a fistula (38) which is formed in a patient's abdominal wall (36) and internal organ wall (37); a supply tube (20, 40), which comprises a tubular element that is disposed in such a way as to be joined to the extracorporeal fixing part and to have a tip-end section extending from the fistula towards the inside of the internal organ, and which has a main lumen (21) formed inside and a sub-lumen (22, 41, 42) formed inside a peripheral wall part; and an intracorporeal fixing part (30) which is provided at the tip-end outer periphery of the supply tube and inflates inside the internal organ when a fluid is fed therein by way of the sub-lumen; and the intracorporeal fixing part comprises an inner balloon (31, 43) and an outer balloon (32, 44) provided on the outer peripheral side of the inner balloon, which each communicate with the sub-lumen by way of injection ports (22a, 22b, 41a, 42a) provided in the peripheral surface of the supply tube, wherein a space is formed between the inner balloon and outer balloon when they are inflated; and a one-way valve (23, 24, 45, 46) is provided in the injection port (22a, 41a) which provides communication between the sub-lumen and the inner balloon, and in the injection port (22b, 42a) which provides communication between the sub-lumen and the outer balloon so that the inner balloon and outer balloon can be filled with the fluid from the sub-lumen by way of the respective one-way valves.

With the fistula catheter according to one or more aspects of the present invention, the intracorporeal fixing part comprises a two-layer balloon formed by the inner balloon and the outer balloon. One-way valves, which provide communication between the sub-lumen and the inner balloon and outer balloon by way of respective injection ports provided in the peripheral surface of the supply tube, are provided in each of the injection ports in order to allow fluid to be fed into the inner balloon and outer balloon from the sub-lumen, but to prevent a return flow. This means that even if fluid escapes from either one of the inner balloon or outer balloon which has been filled with fluid, or either one of the inner balloon or outer balloon deflates due to rupturing, the other can be maintained in an inflated state, so it is possible to prevent the fistula catheter from being removed from the fistula. Moreover, the inflated size of the inner balloon is set to a size which can prevent the fistula catheter from being removed from the fistula.

In this case, the fluid which has filled the inner balloon is still retained inside the outer balloon even if the inner balloon ruptures, and therefore there is essentially no change in the inflated state of the outer balloon. In addition, the intracorporeal fixing part is formed by a two-layer balloon so it is possible to delay the outward escape of the fluid filling the inside. Moreover, the fluid filling the inner balloon and outer balloon is a liquid or gas, and any fluid which is not harmful to the human body may be used, but the use of distilled water is preferred. Furthermore, the volume of the inner balloon is preferably greater than the volume of the outer balloon.

Another structural feature of the fistula catheter according to one or more aspects of the present invention lies in the fact that the one-way valve (23, 45) provided in the injection port which provides communication between the sub-lumen and the inner balloon allows the fluid to pass more easily than the one-way valve provided in the injection port (24, 46) which provides communication between the sub-lumen and the outer balloon.

According to one or more aspects of the present invention, the inner balloon is preferentially filled with the fluid ahead of the outer balloon, so it is possible to avoid the outer balloon being filled first and the inner balloon no longer being able to inflate sufficiently due to the restriction of the inflated outer balloon. The inner balloon and outer balloon can therefore both be inflated to a suitable size. For example, the one-way valve comprises or consists of a film-like valve provided with a slit in the centre, which projects from the injection port into the inner balloon or outer balloon, and fluid can pass through from the sub-lumen into the inner balloon or outer balloon, but it is possible to ensure that the fluid cannot pass through in the other direction.

In this case, if the one-way valve on the inner balloon side is made of a softer material than the one-way valve on the outer balloon side, or the one-way valve on the inner balloon side is larger than the one-way valve on the outer balloon side, it is possible to ensure that the one-way valve on the inner balloon side allows the fluid to pass more easily than the one-way valve on the outer balloon side. That is to say, the one-way valve on the inner balloon side opens under a smaller pressure than the one-way valve on the outer balloon side if the one-way valve on the inner balloon side is made of a softer material than the one-way valve on the outer balloon side. Furthermore, the one-way valve on the inner balloon side opens under a smaller pressure than the one-way valve on the outer balloon side while also allowing a greater amount of fluid to pass therethrough if the one-way valve on the inner balloon side is larger than the one-way valve on the outer balloon side.

A further structural feature of the fistula catheter according to one or more aspects of the present invention lies in the fact that the inner balloon is made of a material which is sparingly stretchable and the outer balloon is made of a material which is more stretchable than the inner balloon.

According to one or more aspects of the present invention, when the outer balloon is filled with fluid after the inner balloon has been filled with fluid and the inner balloon has been inflated to a prescribed size, the outer balloon can be further inflated outside the inner balloon. The inner balloon and the outer balloon can therefore both be inflated to a sufficient size.

Yet another structural feature of the fistula catheter according to one or more aspects of the present invention lies in the fact that the inflated size of the inner balloon is fixed. According to one or more aspects of the present invention, the fixed size of the inflated inner balloon can be set at the minimum size which makes it possible to prevent removal of the fistula catheter from the fistula, for example. As a result, it is possible to reliably prevent the fistula catheter from being removed from the fistula even if the outer balloon ruptures. The intracorporeal fixing part can therefore be sufficiently inflated to the required size.

Furthermore, a further structural feature of the fistula catheter according to one or more aspects of the present invention lies in the fact that the inner balloon and the outer balloon are each fixed to the supply tube by means of adhesive, and the positions, in the direction of extension of the supply tube, of adhesion parts (31a, 31b) of the inner balloon and adhesion parts (32a, 32b) of the outer balloon with respect to the supply tube, are offset.

According to one or more aspects of the present invention, the adhesion parts of the supply tube and the inner balloon, and the adhesion parts of the supply tube and the outer balloon do not project towards the outer periphery of the supply tube in an overlying state. Consequently, even if the intracorporeal fixing part comprises a two-layer balloon formed by the inner balloon and outer balloon, it is possible to prevent, as far as possible, increased resistance when the intracorporeal fixing part is inserted into the fistula together with the supply tube.

DETAILED DESCRIPTION

Figure 1:
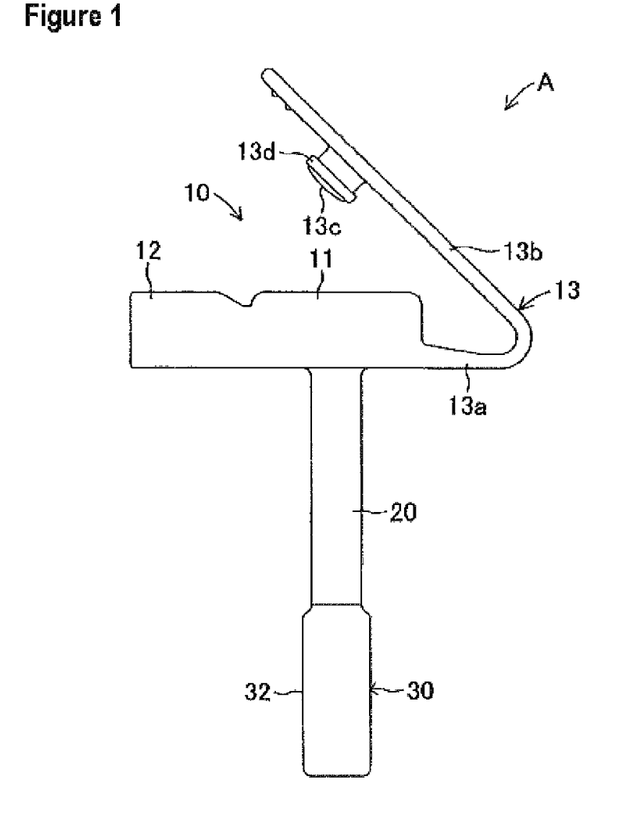
FIG. 1 is a side view showing a fistula catheter according to one mode of embodiment of the present invention.
Figure 2:
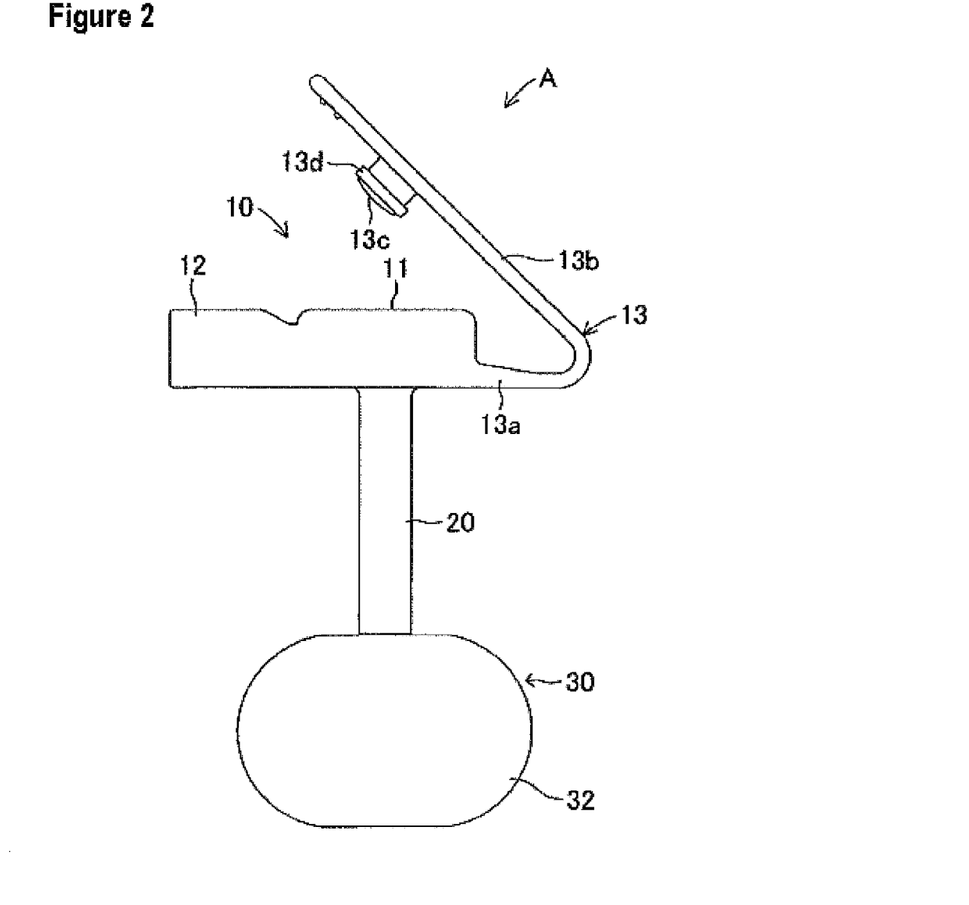
FIG. 2 is a side view showing the situation when the intracorporeal fixing part of the fistula catheter shown in FIG. 1 has been inflated.

One mode of embodiment of the fistula catheter according to one or more aspects of the present invention will be described in detail below with the aid of the figures. FIGS. 1 and 2 show a fistula catheter A according to this mode of embodiment. The fistula catheter A comprises an extracorporeal fixing part 10, a supply tube 20 which is joined to the lower end of the extracorporeal fixing part 10, and an intracorporeal fixing part 30 which is attached to the lower part of the supply tube 20. The extracorporeal fixing part 10 is made of polyurethane or silicone rubber, the supply tube 20 is made of silicone rubber, and the intracorporeal fixing part 30 is made of polyurethane or silicone rubber. In the following description, the directions "front/rear", "left/right" and "up/down" are based on FIGS. 1 and 2.

Figure 3:
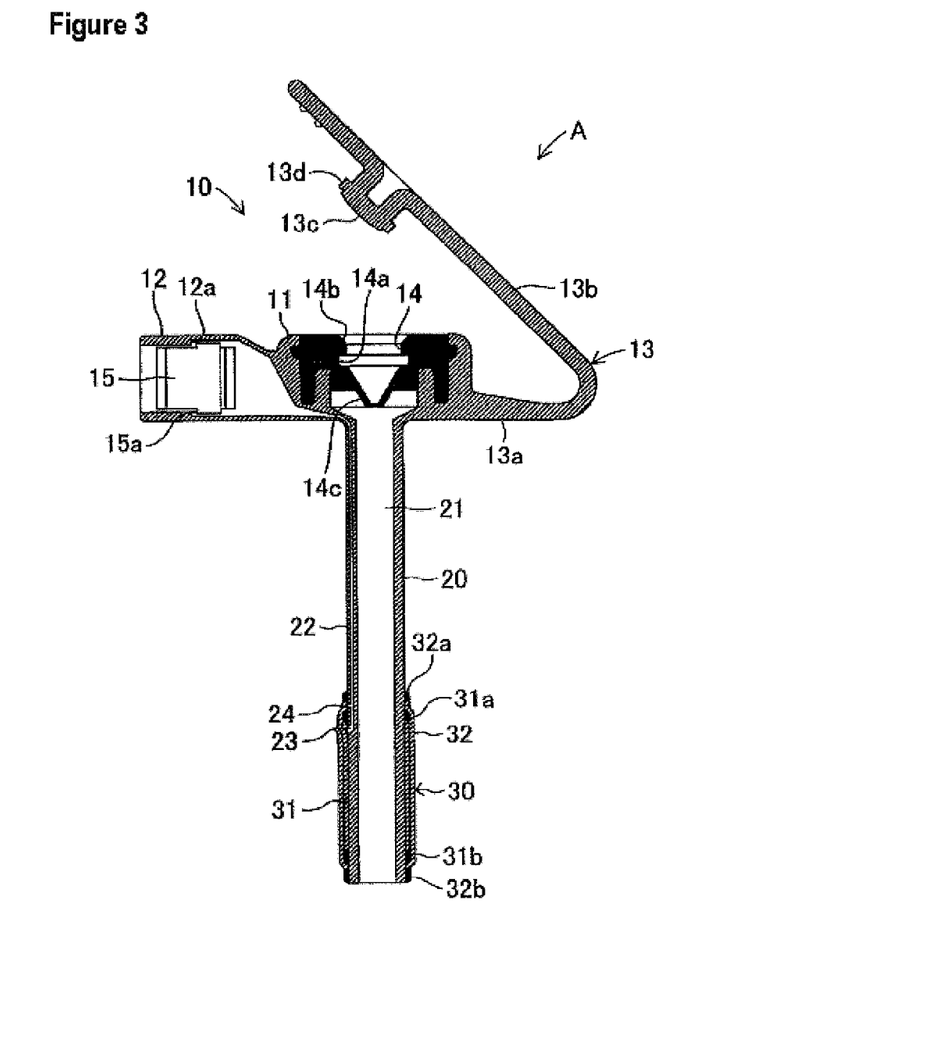
FIG. 3 is a view in cross section of the fistula catheter shown in FIG. 1.
Figure 4:
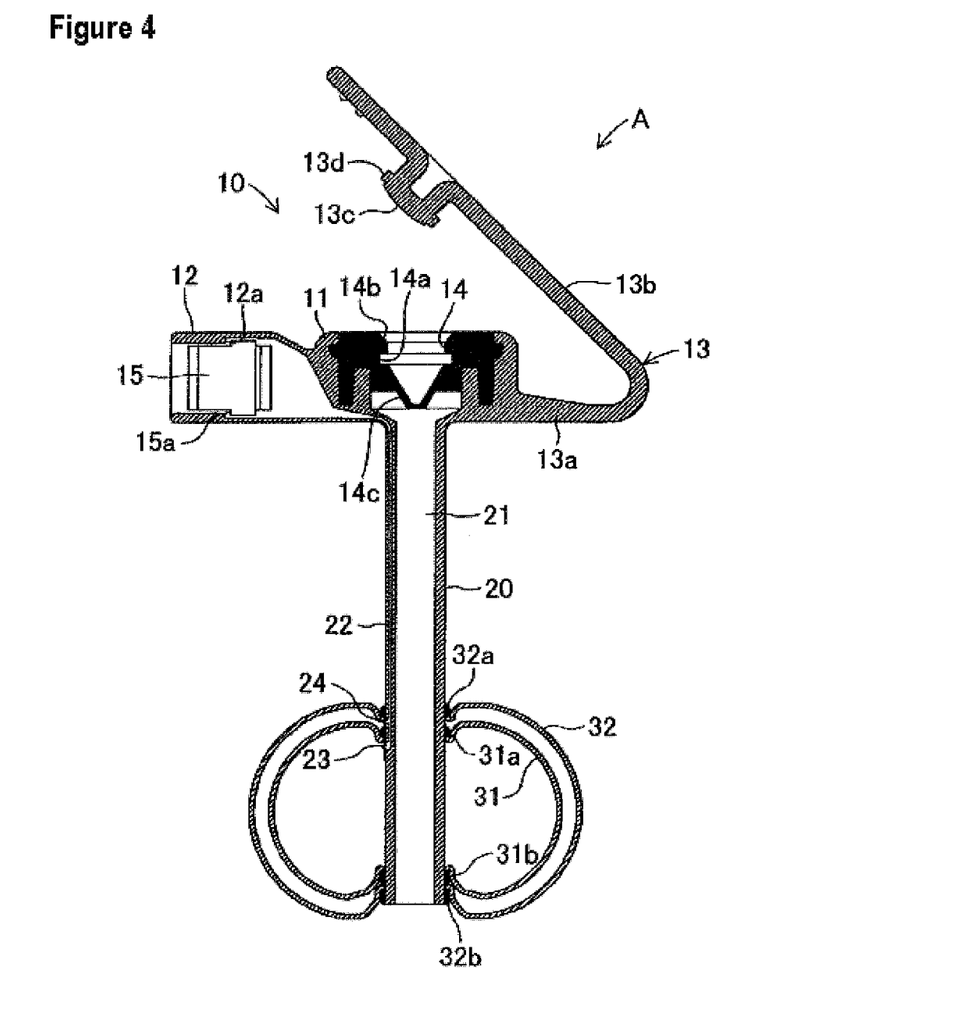
FIG. 4 is a view in cross section showing the fistula catheter shown in FIG. 2.

As shown in FIGS. 3 and 4, the extracorporeal fixing part 10 comprises: a holding part body 11 which is formed in the shape of a ring having a fairly thick wall; a side port 12 which projects horizontally to the left from the left-hand side of the holding part body 11; and an elongate cover part 13 which projects to the right from the lower part on the right-hand side of the holding part body 11. An opening 14 is formed in the centre of the holding part body 11 running vertically therethrough, and an engaging groove part 14a is formed around the circumference in the centre in the vertical direction of the peripheral surface of the opening 14. Furthermore, the upper part of the opening 14 comprises an inclined part 14b which becomes larger in diameter from the upper part towards the lower part, and a one-way valve 14c which projects downwards is formed in the lower part of the opening 14. This one-way valve 14c is formed by a valve provided with a slit (not depicted), and it allows the downward passage of a fluid such as liquid food, nutrients, drugs and water from above inside the holding part body 11, but prevents the return flow of the fluid such as liquid food, nutrients, drugs and water.

The side port 12 has a cylindrical shape and the upper part of the section on the holding part body 11 side comprises an inclined part which extends downwards towards the right. Furthermore, the diameter of the inner peripheral surface of the side port 12 is slightly greater in the right-hand section than in the left-hand section, and a step part 12a is formed at the boundary thereof. An injection valve 15 is disposed inside the side port 12 in such a way as to be able to move left and right. The injection valve 15 comprises a tubular valve element which is provided with a difference in level where the right-hand section is greater in diameter than the left-hand section, and a step part 15a is formed at the boundary thereof.

The small-diameter section is then positioned towards the left inside the side port 12 and the large-diameter section is positioned towards the right inside the side port 12, and the injection valve 15 is disposed inside the side port 12 in a mobile manner. Furthermore, when the injection valve 15 is positioned towards the left and the step part 15a has abutted the step part 12a on the inner peripheral surface of the side port 12, the side port 12 is closed off; when the injection valve 15 is moved to the right from this state, a gap is formed with the inner peripheral surface of the side port 12, and the side port 12 is opened. Furthermore, a spring member is placed between the side part of the holding part body 11 inside the side port 12 and the injection valve 15, and the injection valve 15 is urged to the left in order to close the side port 12 by means of this spring member, although this has been omitted from the figures.

The cover part 13 comprises a linking piece 13a which extends horizontally to the right from the right-hand side of the holding part body 11; a strip-like linking part 13b which is linked to the tip end of the linking piece 13a; and a stopper part 13c which is provided towards the tip end of the strip-shaped linking part 13b. The linking piece 13a is formed by a plate-like portion which does not readily deform, for linking the strip-shaped linking part 13b to the side part of the holding part body 11, and it has the function of preventing the fistula catheter A from being pulled inside the internal organ together with the holding part body 11. The strip-shaped linking part 13b is flexible and can bend in such a way as to rotate up and down about the connection with the linking piece 13a, and can also bend at a sharp angle. The stopper part 13c is provided on the tip-end section of the strip-shaped linking part 13b.

The stopper part 13c is provided on the strip-shaped linking part 13b in such a way as to face the opening 14 when the strip-shaped linking part 13b is bent so that the tip-end section thereof is positioned on the upper surface of the holding part body 11. The stopper part 13c comprises a short, cylindrical protrusion with a bottom which can fit into the opening 14, and a projection 13d which can detachably engage with the groove part 14a in the opening 14 is provided around the circumference thereof. The groove part 14a and the projection 13d can therefore be engaged by bending the strip-shaped linking part 13b and pressing the stopper part 13c into the opening 14, whereby the opening 14 in the holding part body 11 can be closed off. Furthermore, the opening 14 in the holding part body 11 can be opened by pulling the tip-end section of the strip-shaped linking part 13b in order to release the engagement of the stopper part 13c and the opening 14.

Figure 5:
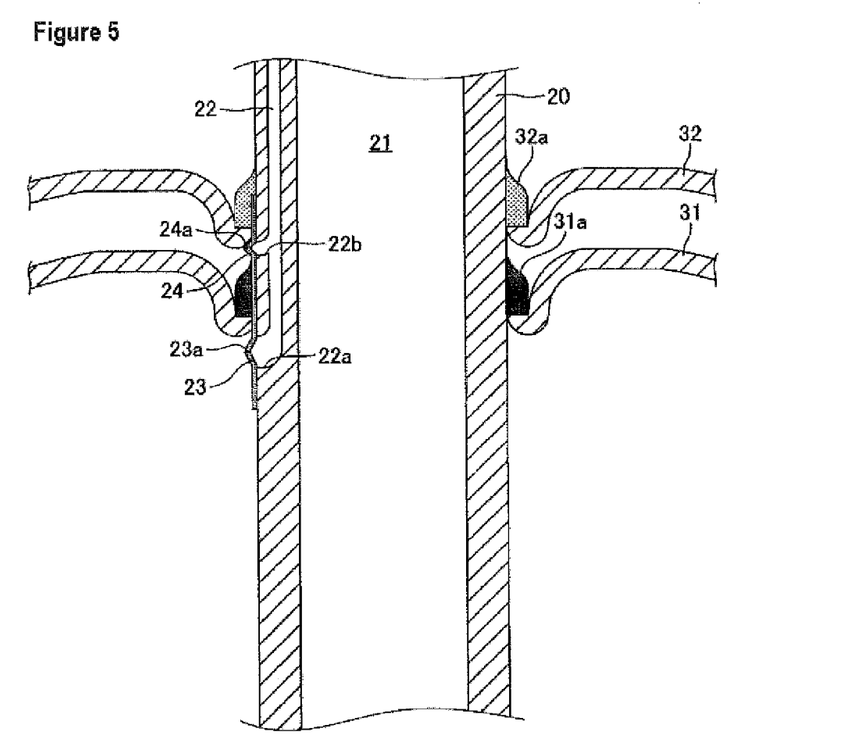
FIG. 5 is an enlarged view in cross section of the adhesion parts of the supply tube and the upper part of the intracorporeal fixing part.

The supply tube 20 comprises or consists of a tubular member in which a main lumen 21 is internally formed in order to supply fluids such as liquid food, nutrients, drugs and water into a patient's stomach, and a sub-lumen 22 is formed in the wall part in order to supply a fluid such as distilled water or air to the intracorporeal fixing part 30. The upper end of the main lumen 21 communicates with the opening 14 by way of the one-way valve 14c of the extracorporeal fixing part 10, while the lower end of the main lumen 21 opens at the lower end of the supply tube 20 and communicates with the outside. Furthermore, the upper end of the sub-lumen 22 communicates with the bottom-right part inside the side port 12, while the lower end of the sub-lumen 22 curves and opens towards the outer peripheral surface in a region on the outer peripheral surface of the supply tube 20 slightly below the centre in the vertical direction thereof. As shown in FIG. 5, this opening forms an injection port 22a. Furthermore, an injection port 22b which communicates with the outside is also formed by bending the sub-lumen 22 towards the outer peripheral surface in a region slightly above the injection port 22a at the lower end. The diameter of the injection port 22a is set to be greater than the diameter of the injection port 22b.

One-way valves 23, 24 can then be formed in the injection ports 22a, 22b, respectively. The one-way valves 23, 24, for example, can have a structure in which slits 23a, 24a are respectively provided at the tip ends of beak-like protrusions which project outwards, and fluid is allowed to pass from inside the sub-lumen 22 towards the outside, but the fluid is prevented from passing from the outside towards the inside of the sub-lumen 22. Furthermore, the one-way valves 23, 24 can be both made of silicone rubber, but the one-way valve 23 positioned below is formed to be larger than the one-way valve 24 positioned above so as to open under a smaller pressure. The one-way valve 23 therefore enables the fluid to pass through more quickly and in a larger amount than the one-way valve 24.

The intracorporeal fixing part 30 is typically provided between a region on the outer peripheral surface of the supply tube 20 slightly above the region where the one-way valve 24 is provided, and the lower end of the supply tube 20. The intracorporeal fixing part 30 typically comprises an inner balloon 31 and an outer balloon 32; the inner balloon 31 can be made of polyurethane and the outer balloon 32 can be made of silicone rubber. It should be noted that polyurethane and silicone rubber typically have excellent formability, drug resistance and biocompatibility, while also having properties whereby water escape (gas escape) is relatively unlikely to occur, and therefore polyurethane and silicone rubber are selected as the materials from which the intracorporeal fixing part 30 is made. The inner balloon 31 can be provided between the region on the outer peripheral surface of the supply tube 20 lying in between the region where the one-way valve 23 is provided and the region where the one-way valve 24 is provided, and a region slightly above the lower end of the supply tube 20; the inner balloon 31 can comprise a slightly stretchable, substantially bag-shaped element which is formed with a vertical hole.

Furthermore, the inner balloon 31 covers the outer peripheral surface of the supply tube 20 and is fixed to the supply tube 20 by bonding the upper and lower ends of the inner peripheral surface to the outer peripheral surface of the supply tube 20 by means of adhesive; the inner balloon 31 is inflated by being filled with fluid from the sub-lumen 22, by way of the injection port 22a and the one-way valve 23, as shown in FIG. 4. In this process, the inner balloon 31 expands in a substantially spherical shape which is somewhat longer in the left/right direction and the front/rear direction than in the up/down direction, and adhesion parts 31a, 31b of the inner balloon 31 which adhere to the supply tube 20 become embedded in the upper part and lower part of the inflated inner balloon 31. Furthermore, the inner balloon 31 can be inflated to a fixed size, for example a size which is the minimum for maintaining the fistula catheter A in an indwelling state in the fistula.

The outer balloon 32 is provided between a region on the outer peripheral surface of the supply tube 20 slightly above the region where the one-way valve 24 is provided, and the lower end of the supply tube 20, and comprises a cylindrical element which is more stretchable than the inner balloon 31. The outer balloon 32 covers the inner balloon 31 and is fixed to the supply tube 20 by bonding the upper and lower ends of the inner peripheral surface to the outer peripheral surface of the supply tube 20 in regions above and below the inner balloon 31.

An upper adhesion part 32a of the outer balloon 32 which adheres to the supply tube 20 is positioned above the adhesion part 31a of the inner balloon 31, and a lower adhesion part 32b of the outer balloon 32 which adheres to the supply tube 20 is positioned below the adhesion part 31b of the inner balloon 31. When the outer balloon 32 has not been expanded prior to inflation, it crushes the inner balloon 31 by pressing it against the outer peripheral surface of the supply tube 20, and the outer balloon 32 maintains a cylindrical state, as shown in FIGS. 1 and 3. Furthermore, the outer balloon 32 is inflated by being filled with fluid from the sub-lumen 22 by way of the injection port 22b and the one-way valve 24, as shown in FIGS. 2 and 4. In this process, the outer balloon 32 inflates in a substantially spherical shape which is longer in the left/right direction and front/rear direction than in the up/down direction, and the adhesion parts 32a, 32b of the outer balloon 32 become embedded in the upper part and lower part of the inflated outer balloon 32.

Figure 6:
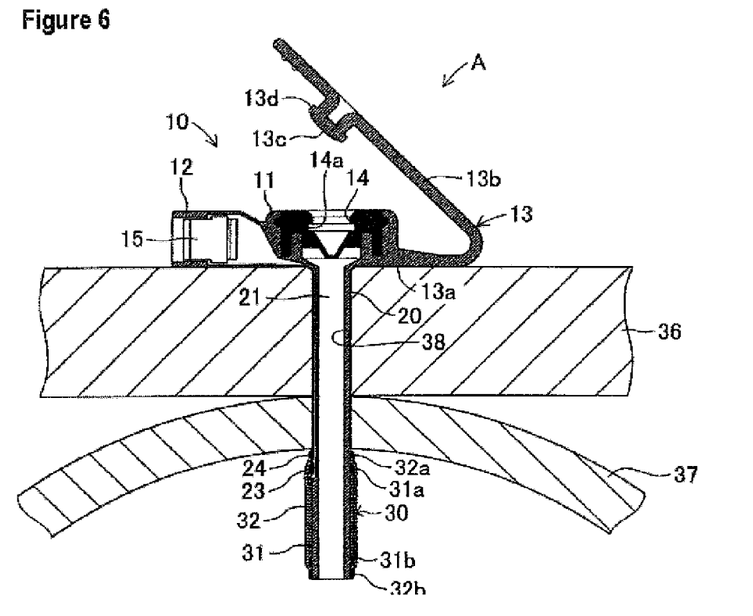
FIG. 6 is a view in cross section showing the situation when the fistula catheter has been inserted into a fistula.

When the fistula catheter A having this structure is used, the fistula catheter A in which the intracorporeal fixing part 30 is not expanded is first of all passed through a fistula 38 which is formed in the patient's abdominal wall 36 and stomach wall 37, as shown in FIG. 6. At this point, the outer balloon 32 crushes the inner balloon 31 to form a cylindrical shape, and the adhesion parts 32a, 32b of the outer balloon 32 and the adhesion parts 31a, 31b of the inner balloon 31 are in different positions on the outer peripheral surface of the supply tube 20. The intracorporeal fixing part 30 is therefore not bulky overall and is in a state of close contact with the outer peripheral surface of the supply tube 20, so the supply tube 20 and the intracorporeal fixing part 30 can be made to smoothly pass inside the fistula 38.

Once the intracorporeal fixing part 30 has entered to inside the stomach wall 37, the injection port of an injector (not depicted) for injecting distilled water which is one type of fluid is inserted into the side port 12, and distilled water is injected from the injector into the inner balloon 31 and outer balloon 32 by way of the sub-lumen 22. In this process, the injection valve 15 is pressed by the injection port of the injector and moved towards the holding part body 11 in resistance to the spring member, and the distilled water supplied from the injector passes through the gap between the side port 12 and the injection valve 15, and enters the sub-lumen 22. The distilled water then passes through the one-way valves 23, 24 and enters the inside of the inner balloon 31 and the outer balloon 32.

When the inner balloon 31 and outer balloon 32 are filled with distilled water, most of the distilled water fed to the sub-lumen 22 from the injector is first of all supplied into the inner balloon 31 from the one-way valve 23, and the inner balloon 31 inflates to a prescribed size. Then, when the water pressure inside the inner balloon 31 rises and the water pressure inside the sub-lumen 22 also rises, distilled water is also supplied into the outer balloon 32 from the one-way valve 24 and the outer balloon 32 also inflates. As a result, the inner balloon 31 is inflated to a size which makes it possible to prevent the fistula catheter A from being withdrawn from the fistula 38, and the outer balloon 32 is also inflated while a gap is maintained with the inner balloon 31.

Figure 7:
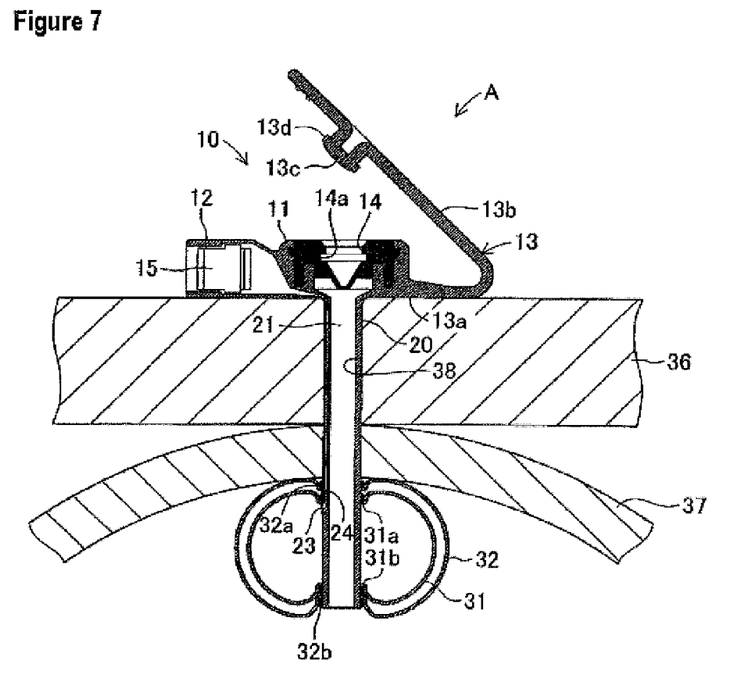
FIG. 7 is a view in cross section showing the situation when the intracorporeal fixing part of the fistula catheter shown in FIG. 6 has been inflated.

By this means, the upper surface of the outer balloon 32 comes into contact with the inner surface of the stomach wall 37, as shown in FIG. 7. As a result, the fistula catheter A is prevented from being withdrawn from the fistula 38 and remains fitted in the patient's abdominal region. Here, the adhesion part 32a of the outer balloon 32 is not in contact with the stomach wall 37, and it is only the curved portion at the top of the outer balloon 32 which is in contact with the stomach wall 37.

When the fistula catheter A is indwelling in the fistula 38, the injector is pulled out from the side port 12. This causes the injection valve 15 to move to the opening side of the side port 12 due to the elasticity of the spring member, thereby closing off the side port 12. The inner balloon 31 and outer balloon 32 remain inflated due to the action of the injection valve 15 in closing off the side port 12 and the action of the one-way valves 23, 24 in preventing a return flow of distilled water from the inner balloon 31 and outer balloon 32 to the sub-lumen 22. In this instance, the inner balloon 31 and outer balloon 32 remain inflated even if an external force is applied to the outer balloon 32 by contact of the stomach wall 37 with the outer balloon 32 due to peristaltic movement of the stomach, or similar.

Then, when fluids such as liquid food, nutrients, drugs and water are taken in by the patient, a fluid supply tube (not depicted) is connected to the opening 14 of the extracorporeal fixing part 10 which is in an open state. In this state, a fluid is introduced into the fluid supply tube from the end opening of the fluid supply tube. As a result, the fluid enters the opening 14 from the fluid supply tube and passes through the one-way valve 14c, after which it is supplied into the patient's stomach by way of the main lumen 21. Furthermore, after the fluid has been supplied, the fluid supply tube is removed from the extracorporeal fixing part 10 and the opening 14 in the extracorporeal fixing part 10 is closed by the stopper part 13c of the cover part 13. By this means, return flow of the fluid supplied into the stomach is prevented by means of the one-way valve 14c and the stopper part 13c.

The adhesion part 32a of the outer balloon 32 is thus not in contact with the stomach wall 37, and it is only the curved portion at the top of the outer balloon 32 which is in contact with the stomach wall 37 while the fistula catheter A is indwelling in the fistula 38, so it is possible to prevent the outer balloon 32 from irritating the stomach wall 37 and causing ulcers, and also to prevent the stomach wall 37 from being damaged. Furthermore, the adhesion part 32b does not come into contact with the stomach wall 37 and it is only the curved portion at the bottom of the outer balloon 32 which comes into contact with the stomach wall 37, even if the stomach shrinks when the patient is hungry and the stomach wall 37 at the lower part of the stomach comes into contact with the outer balloon 32; it is therefore possible to prevent the outer balloon 32 from irritating the stomach wall 37 and causing ulcers, and also to prevent the stomach wall 37 from being damaged.

The fistula catheter A is used in the manner described above, and there are also times when the outer balloon 32 deteriorates and ruptures during the usage period. In such cases also, the inner balloon 31 is maintained in an inflated state, so the fistula catheter A is not removed from the fistula 38 and is maintained in a state in which it can be used. Furthermore, it is distilled water which spills out from inside the ruptured outer balloon 32, so the patient is not harmed even if distilled water enters the stomach. Furthermore, if the inner balloon 31 ruptures or if there is a leak from the inner balloon 31, the distilled water inside the inner balloon 31 is held as it is inside the outer balloon 32, so there are no problems in particular.

With the fistula catheter A according to this mode of embodiment, the intracorporeal fixing part 30 thus comprises a two-layer balloon formed by the inner balloon 31 and the outer balloon 32. This means that, at the least, water is unlikely to escape spontaneously to the outside from the inner balloon 31, and the inner balloon 31 is maintained in an inflated state, so it is possible to prevent the fistula catheter A from being removed from the fistula 38. Furthermore, the one-way valves 23, 24 can be provided at the boundary parts of the sub-lumen 22 with the inner balloon 31 and the outer balloon 32, so even if water escapes from either one of the inner balloon 31 or the outer balloon 32 or a rupture occurs therein causing deflation, the other can be maintained in an inflated state, and therefore it is possible to prevent the fistula catheter A from being removed from the fistula 38.

Furthermore, the one-way valve 23 is larger than the one-way valve 24, which means that the one-way valve 23 allows the distilled water to pass through under a smaller pressure than the one-way valve 24. The inner balloon 31 is therefore preferentially filled with distilled water ahead of the outer balloon 32. This makes it possible to avoid the outer balloon 32 being filled first and the inner balloon 31 no longer being able to inflate sufficiently due to the restriction of the inflated outer balloon 32. As a result, the inner balloon 31 and outer balloon 32 can both be inflated to a suitable size. It is thus possible to inflate both the inner balloon 31 and the outer balloon 32 to a suitable size even though the two injection ports 22a, 22b are in communication with one sub-lumen 22.

In addition, the inner balloon 31 is made of polyurethane which is sparingly stretchable, while the outer balloon 32 is made of silicone rubber which is highly stretchable, so the inside of the inner balloon 31 is filled with distilled water and the inner balloon 31 is inflated to a prescribed size, and then when the inside of the outer balloon 32 is filled with distilled water, the outer balloon 32 is further inflated outside the inner balloon 31. Consequently, both the inner balloon 31 and the outer balloon 32 can be inflated to a sufficient size.

Furthermore, the size of the inflated inner balloon 31 is typically fixed, so the inner balloon 31 can be sufficiently inflated to the required size. In addition, the adhesion parts 31a, 31b of the inner balloon 31 and the adhesion parts 32a, 32b of the outer balloon 32 can be provided in different positions on the outer peripheral surface of the supply tube 20, and therefore the adhesion part 31a and adhesion part 32a, and the adhesion part 31b and adhesion part 32b do not become bulky by lying one over another, and the supply tube 20 and intracorporeal fixing part 30 can smoothly pass through the inside of the fistula 38.

Figure 8:
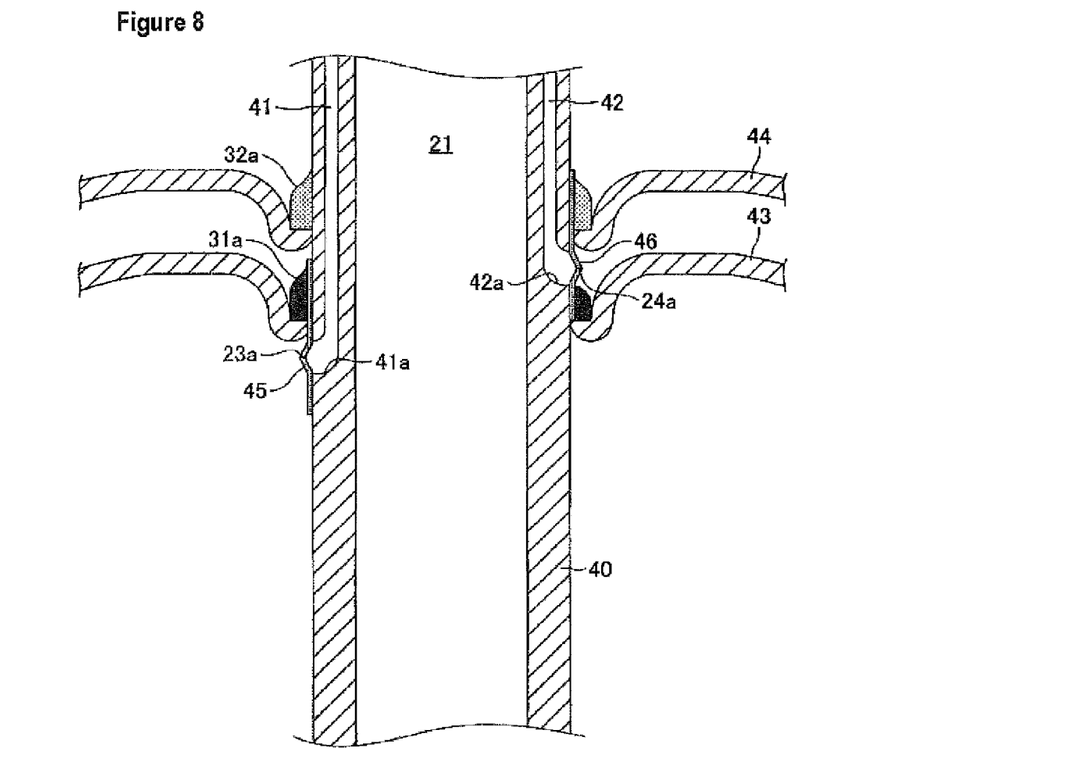
FIG. 8 is an enlarged view in cross section of the adhesion parts of the supply tube and the upper part of the intracorporeal fixing part, in a fistula catheter according to another mode of embodiment of the present invention.

FIG. 8 shows the main parts of a fistula catheter according to another mode of embodiment of one or more aspects of the present invention. In this fistula catheter, two sub-lumens 41, 42 can be formed in a supply tube 40. The sub-lumen 41 is provided in the left-hand part of the supply tube 40, and the lower end thereof communicates with the inside of an inner balloon 43 by way of an injection port 41a. Furthermore, the sub-lumen 42 is provided in the right-hand part of the supply tube 40, and the lower end thereof communicates with the inside of an outer balloon 44 by way of an injection port 42a. The injection port 41a at the lower end of the sub-lumen 41 and the injection port 42a at the lower end of the sub-lumen 42 can be formed to be the same size.

Furthermore, a one-way valve 45 provided in the injection port 41a and a one-way valve 46 provided in the injection port 42a can also formed to be the same size. The one-way valves 45, 46 can be both made of silicone rubber, but the one-way valve 45 is made of softer silicone rubber than the one-way valve 46. The one-way valve 45 therefore allows fluids, including distilled water or air etc., to pass through under a smaller pressure than the one-way valve 46. Furthermore, the upper end of the sub-lumen 42 communicates with the sub-lumen 41 at the upper end of the supply tube 40. The structures of the other elements of this fistula catheter can be the same as those of the fistula catheter A described above. Elements which can be the same therefore bear the same reference symbols and will not be described again.

In accordance with this fistula catheter, the inner balloon 43 and outer balloon 44 can both be inflated to a suitable size, even though the injection ports 41a and 42a communicate with the two sub-lumens 41, 42, respectively. The other actions and effects of this fistula catheter are typically the same as the actions and effects of the fistula catheter A described above.

Furthermore, the fistula catheter according to one or more aspects of the present invention is not limited to the modes of embodiment described above, and it may still be implemented with suitable modifications. For example, in the modes of embodiment described above, distilled water is used in order to inflate the inner balloon 31, 43 and outer balloon 32, 44, but air may equally be used instead of distilled water, or another liquid or gas which is not harmful to the human body may equally be used. Furthermore, the fistula catheter is not limited to an arrangement in which the extracorporeal fixing part 10 is joined to the upper end of the supply tube 20, 40, and an arrangement in which a flange-shaped extracorporeal fixing part is joined to an intermediate part of a long supply tube is equally feasible. In addition, in the modes of embodiment described above, the internal organ involved is the stomach, but the internal organ is not limited to the stomach, and it may equally be the kidneys or bladder etc. Furthermore, it is also possible to suitably change the materials from which each of the elements of the fistula catheter A are made.

KEY TO SYMBOLS

10 . . . extracorporeal fixing part; 20, 40 . . . supply tube; 21 . . . main lumen; 22, 41, 42 . . . sub-lumen; 22a, 22b, 41a, 42a . . . injection port; 23, 24, 45, 46 . . . one-way valve; 30 . . . intracorporeal fixing part; 31, 43 . . . inner balloon; 31a, 31b, 32a, 32b . . . adhesion part; 32, 44 . . . outer balloon; 36 . . . abdominal wall; 37 . . . stomach wall; 38 . . . fistula; A . . . fistula catheter.

The invention claimed is:

1. A fistula catheter to be disposed in a fistula of a patient, comprising:
    an extracorporeal fixing part configured to be disposed on an abdominal wall surface-side of the fistula;
    a supply tube comprising a tubular element joined to the extracorporeal fixing part, and having a tip-end section, a main lumen, and a sub-lumen in a peripheral wall thereof; and
    an intracorporeal fixing part at an outer periphery of the supply tube and proximate the tip-end section, the intracorporeal fixing part comprising an inner balloon and an outer balloon outside of the inner balloon, a first one-way valve disposed between the sub-lumen and the inner balloon, and a second one-way valve disposed between the sub-lumen and the outer balloon, the inner balloon in communication with the sub-lumen through the first one-way valve, and the outer balloon in communication with the sub-lumen through the second one-way valve.

2. The fistula catheter according to claim 1, further comprising a first injection port in the sub-lumen and a second injection port in the sub-lumen, wherein the first one-way valve is disposed in the first injection port and the second one-way valve is disposed in the second injection port.

3. The fistula catheter according to claim 2, wherein the outer balloon is comprised of a material that is more stretchable than the inner balloon material comprising the inner balloon.

4. The fistula catheter according to claim 3, wherein the inner balloon has fixed inflation size.

5. The fistula catheter according to claim 4, wherein the inner balloon and the outer balloon are each fixed to the supply tube by adhesive.

6. The fistula catheter according to claim 3, wherein the first one-way valve and the second one-way valve are configured to operate at pressures different from one another such that the inner balloon is inflated via the sub-lumen in advance of the outer balloon being inflated via the sub-lumen.

7. The fistula catheter according to claim 1, wherein, when each of the inner balloon and the outer balloon is inflated, a space is formed therebetween.

8. The fistula catheter according to claim 1, wherein each of the first balloon and the second balloon are inflated via the sub-lumen.

9. The fistula catheter according to claim 1, wherein the first one-way valve is sized and configured to open at first pressure to permit fluid flow from the sub-lumen to inflate the inner balloon,
    wherein the second one-way valve is sized and configured to open at second pressure to permit fluid flow from the sub-lumen to inflate the outer balloon, and
    wherein the first pressure is a different pressure than the second pressure.

10. The fistula catheter according to claim 1, wherein the first pressure is lower than the second pressure.

11. The fistula catheter according to claim 1, wherein the first one-way valve and the second one-way valve are configured to operate at pressures different from one another such that the inner balloon is inflated via the sub-lumen in advance of the outer balloon being inflated via the sub-lumen.

* * * * *